United States Patent [19]
Elias

[11] Patent Number: 5,632,093
[45] Date of Patent: May 27, 1997

[54] INDUCTIVE SENSOR AND METHOD FOR DETECTING DISPLACEMENT OF A BODY

[76] Inventor: Sharon A. Elias, 420 E. 72nd St., No. 8-K, New York, N.Y. 10021

[21] Appl. No.: 359,888

[22] Filed: Feb. 14, 1995

Related U.S. Application Data

[63] Continuation-in-part of Ser. No. 245,156, May 17, 1994, Pat. No. 5,456,013, which is a continuation-in-part of Ser. No. 95,579, Jul. 19, 1993, abandoned.

[51] Int. Cl.$^6$ .................................................. G01C 9/06
[52] U.S. Cl. .......................... 33/366; 33/513; 433/27
[58] Field of Search ..................... 33/356, 365, 366, 33/377, 513; 128/776, 777; 324/207.15, 207.23, 207.24, 207.25; 336/135, 136; 433/27, 72

[56] References Cited

U.S. PATENT DOCUMENTS

| | | | |
|---|---|---|---|
| 3,184,861 | 5/1965 | Conard | 33/366 |
| 3,235,790 | 2/1966 | Collins | 336/136 |
| 3,839,904 | 10/1974 | Stripling et al. | 33/366 |
| 3,911,592 | 10/1975 | Crask | 33/366 |
| 3,984,918 | 10/1976 | Chaney | 33/366 |
| 4,507,965 | 4/1985 | Stratton et al. | 33/366 |
| 4,660,290 | 4/1987 | Hori et al. | 33/366 |
| 4,821,423 | 4/1989 | Adams | 33/366 |
| 4,945,274 | 7/1990 | Pempeintner | 336/135 |
| 4,991,301 | 2/1991 | Hore | 33/366 |
| 5,079,847 | 1/1992 | Swartz et al. | 33/366 |
| 5,452,520 | 9/1995 | Raj et al. | 33/366 |
| 5,456,013 | 10/1995 | Elias | 33/366 |

Primary Examiner—Christopher W. Fulton
Assistant Examiner—G. Bradley Bennett
Attorney, Agent, or Firm—Amster, Rothstein & Ebenstein

[57] ABSTRACT

An inductive sensor is comprised of a sealed housing; at least one current path disposed in the housing; means for applying current to the current path; variable low reluctance magnetic path about the current path; and means for sensing the output from the current path as a function of variations in the magnetic flux path. Alternative current path configurations include a differential transformer, comprised of a permanent magnet or one or more primary coils in conjunction with two secondary coils, or a voltage divider, comprised of two primary coils. The variable magnetic flux path includes ferromagnetic fluid disposed in the housing to a level at which all coils are at least partially submersed. Tilt or other displacement of the sensor results in a change in the amount of fluid contacting the coils and a resultant change in current output from the current path means. The change in sensed voltage is indicative of displacement and sustained output voltage is proportional to the degree of tilt of the sensor.

12 Claims, 11 Drawing Sheets

INDUCTIVE SENSOR AND METHOD FOR DETECTING DISPLACEMENT OF A BODY

This is a continuation application of Ser. No. 08/245,156 May 17, 1994 now U.S. Pat. No. 5,456,013, which was a continuation-in-part application of Ser. No. 08/095,579, filed Jul. 19, 1993 now abandoned.

FIELD OF THE INVENTION

The invention relates generally to the field of sensing the tilt or displacement of a body. More specifically, it relates to the precise measurement of the single or multi-axis angular displacement of a body, such as a tooth or dental implant anchor. Further, it relates to sensing of displacement of a body due to mechanical shock, acceleration, deceleration, etc.

BACKGROUND OF THE INVENTION

A vast number of technological arenas require dynamic sensing of attitude, acceleration, mechanical shock, etc. of a system in order to monitor the instantaneous conditions of the components of that system. For example, in aeronautic applications, measurement of the angular displacement of components due to vibration is critical in evaluating the stress on the components and the possibility of mechanical failure. Similarly, in automotive applications, from engine efficiency and wear to seat belt and air bag weighting and deployment applications, dynamic sensing of acceleration, deceleration and mechanical shock is crucial.

Sensor applications in the medical field are wide-spread as detailed in an article entitled "Sensors Add Smarts to Medical Products" by Mark A. Gottschalk, *Design News*, page 58, Aug. 2, 1993, wherein a variety of motion and other condition sensors are detailed.

In the field of dentistry, it is necessary to measure the mobility or angular displacement of a tooth or dental implant to predict the long term integrity of the tooth or implant. In particular, in preparation for securing a crown to an implanted fixture, the integrity of the implant in the patient's jaw must be tested. Generally, an opening is created in the patient's jaw and a setting for the fixture is inserted into the opening. The setting materials have been developed to be highly compatible with human bone, whereby under ideal circumstances, the patient's bone tissue surrounding the setting osseointegrates and effectively incorporates the setting into the jaw structure. After a reasonable healing period, the integrity of the setting in the jaw is evaluated. If there is any movement of the setting, it is concluded that the setting has not adapted sufficiently to the jaw to support a dental implant. Similarly, for an existing tooth, it may be concluded that the tooth is not sufficiently rooted in the mouth structure to sustain normal use without additional support in the form of bridges, etc.

Available tooth displacement sensors are detailed in the article entitled "Review of Methods for Measuring Tooth Mobility" by Dr. Samuel Yankell, which was published in 1988 in the *Compendium of Continuing Education*, Dental Supplement No. 12, pages S428–S432. As detailed therein, early sensors comprised calipers which recorded the physical displacement of the tooth in response to pressure applied thereto. Assessing the exact amount of pressure to which the tooth is subjected is difficult in such a system. Furthermore, the caliper-based systems were inexact given the fact that the calipers themselves often move in response to the applied pressure, thereby influencing the measurements. Later sensors have been developed to measure tooth mobility without the application of an external force to the tooth and measuring tool. Eddy current displacement sensors, holographic interferometers, and stereophotography systems have been used to measure tooth mobility without the measuring tool physically contacting the tooth and thereby, to some degree, physically influencing the tooth movement. Each of the foregoing systems is able to take a "picture" of the tooth under various load conditions, which conditions simulate either expected dental procedures or normal usage to which the tooth or fixture will be subjected. An analysis of the "pictures" provides a profile of the tooth or fixture mobility. A disadvantage of the latter methods of measurement is the need to rely on an external standard by which the movement observed in successive "pictures" is correlated to actual displacement in response to a load.

In unrelated technologies, tilt sensors have been developed utilizing several basic approaches. Low gravity accelerometers utilizing force balance spring mechanisms provide highly accurate tilt angle measurement; however, such systems are large in size incorporating high cost, complex electromechanical transducers. Though appropriate for large scale tilt or attitude measurements, such as for aeronautic applications, such sensors cannot be scaled to be workable in smaller dimensions.

Another category of angular measurement devices rely on the use of a variable capacitor or variable resistor positioned in an enclosure which is partially filled with either a dielectric or a conductive fluid. Upon angular displacement of the enclosure, the movement of the air bubble above the fluid is detected by measurement of the change in the electrical capacitance or resistance.

An angular displacement sensor is provided in U.S. Pat. No. 3,839,904 of Stripling, et al, which is entitled "Magnetic Fluid Level Detector And Vibration Transducer". The Stripling, et al sensor provides a magnetic fluid sensing element having a primary coil and two secondary coils disposed about a vial which is partially filled with fluid. A single magnetic flux path passes through the primary and the two secondary coils, with a portion of the flux path being in the air gap about the fluid in the vial. Angular displacement of the vial results in displacement of the fluid and a consequent change in the magnetic field, resulting in an output voltage indicative of the displacement. Such a sensor must be relatively large in size in order to compensate for the large presence of an air gap in conjunction with sufficient ferromagnetic fluid for the desired magnetic permeability.

U.S. Pat. No. 4,676,103 of Nakajima provides "Acceleration or Inclination Sensors" which operate in a similar manner to the above-noted category of systems. The Nakajima sensors effectively utilize a bubble of magnetic fluid which is displaced in response to angular displacement of its housing thereby causing a change in the electrical capacity.

A dual axis sensor is provided in U.S. Pat. No. 5,079,847 of Swartz, et al. wherein the capacitances on paired capacitive quadrants of a conductive film are measured as a function of tilt.

Some disadvantages of the sensors which rely in part on the air bubble or air gap in the sensor enclosure include variability in readings due to ambient temperature fluctuations, relatively low output signal levels due to the fact that air is a high reluctance path for magnetic flow, and lack of scalability to ideal dimensions given the need to increase fluid amounts to compensate for the high reluctance air path.

What is desired, therefore, is a system which provides high output signals, representative of angular displacement, in a, temperature stable sensor.

3

What is further desirable is a sensor which can accurately measure displacement at any axial orientation from the horizontal starting position of the sensor.

It is, therefore, an objective of the present invention to provide a system and method for measuring angular displacement of a body on a small scale.

It is another objective of the invention to provide a system and method for measuring angular displacement of a body without requiring external calibration.

It is still another objective of the invention to provide a system and method by which angular displacement of a body can be measured without applying force to the measurement tool itself and thereby affecting the results of the measurement.

Yet another objective of the invention is to provide an angular displacement sensor which can effectively provide high output signals representative of angular displacement in a small-scale, temperature-stable sensor.

It is a further objective of the present invention to provide a tilt sensor whereby tilt can be detected along perpendicular axes of the sensor (i.e., 0° and 180° or 90° and 270°).

It is yet another objective to provide a sensor having a power source which is self-generated by the use of a permanent magnet.

SUMMARY OF THE INVENTION

These and other objectives of the invention are realized by the inventive angular displacement sensor which comprises an AC power source, a sealed housing; at least one current path means disposed in the housing; at least one variable low reluctance magnetic flux path about the current path means; and means for sensing the output from the current path means as a function of variations in the variable flux path. One representative embodiment comprises a variable differential transformer having two primary coils, or at least one primary coil and two secondary coils, means for measuring voltage output from the transformer, and a reservoir of ferromagnetic fluid, which fluid selectively contacts the two coils and, when displaced in proportion to the angular displacement of the body to which the sensor is attached, changes the magnetic flux path and thereby the relative inductance in the coils to produce an output voltage. The output voltage will be indicative of motion due to mechanical shock, etc., and a sustained output voltage will be proportional to the tilt angle and its phase will be indicative of the direction of tilt. The transformer can be mounted on a clamp which is adapted to engage the body, such as the tooth or fixture, for which displacement is to be measured.

BRIEF DESCRIPTION OF THE INVENTION

The invention will now be described with reference to the attached drawings wherein.

4

DETAILED DESCRIPTION OF THE PREFERRED EMBODIMENT

Figure 1:
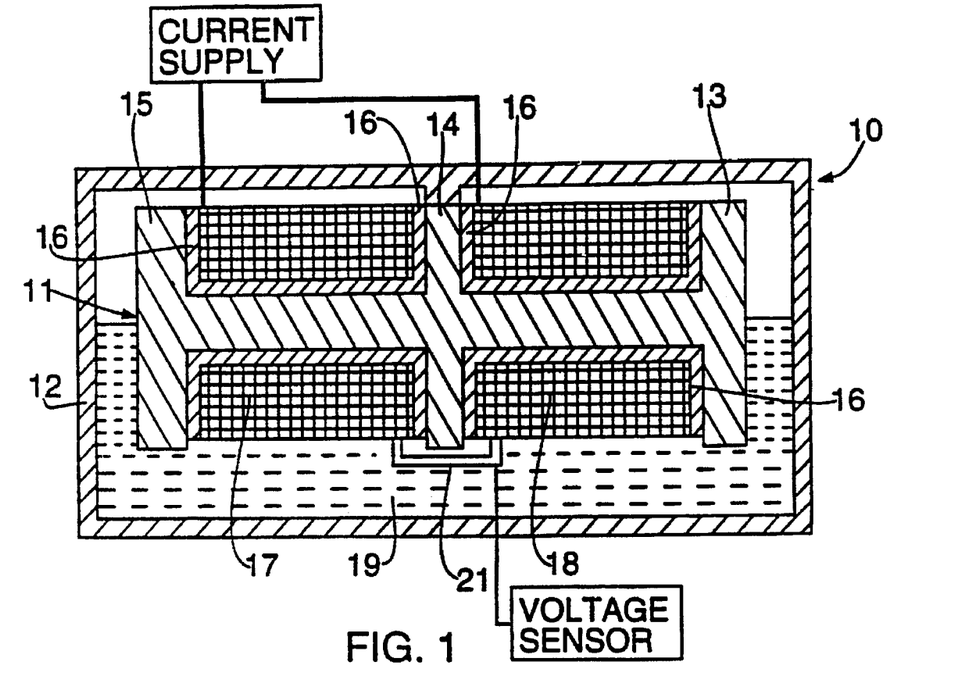
FIG. 1 provides a schematic illustration of a first embodiment of the invention having only first and second primary coils.

A first embodiment of the invention, as illustrated in FIG. 1, is a single axis tilt sensor, 10. The housing, 12, of sensor 10 is a sealed housing which is fabricated of plastic or non-ferromagnetic metal and has a lower edge which is flat with respect to the plane of gravity. An elongated coil form, 11, is disposed in housing 12. The coil form 11 is made of ferromagnetic material, such as iron, ferrite, etc., and is configured to include flanges 13, 14 and 15 extending in the radial direction from the central axis of the form, with at least the center flange 14 being attached to housing 12. A first primary coil 17 of insulated electrically conductive wire is wound about coil form 11 in the opening defined by flanges 15 and 14. A second primary coil 18 of insulated electrically conductive wire is wound about coil form 11 in the opening defined by flanges 14 and 13. Coils 17 and 18 may comprise enamel-coated copper wire and are connected to each other, at junction 21. The primary coils 17 and 18 are preferably connected in series opposition, as will be detailed below in the discussion of the operation of the sensor; although, an alternative embodiment in which the coils are connected in series aiding is also noted. An AC power source (not shown) is connected to supply a current to the sensor coils and a meter (also not shown) is connected to measure the output of the sensor coils as a function of the angular displacement of the sensor.

The openings in the coil form, the first being defined by flanges 15 and 14 and the second being defined by flanges 14 and 13, may each additionally be provided with a bobbin 16 of insulated material such as plastic. The bobbins 16 provide additional insulation between the coil form and the coils and can physically facilitate the placement of the windings of the coils 17 and 18. Housing 12 is sealed and is partially filled with a ferromagnetic fluid 19, to a level at which the coil form 11 is partially submerged in the fluid.

In operation, a source of alternating current is applied to the terminals of coil 17 and coil 18, which are connected at junction 21 in series opposition. The current through coil 17 will generate a magnetic flux in a path about the submerged portion of coil 17 in the opening defined by flanges 15 and 14. The current through coil 18 will generate magnetic flux in a path about the submerged portion of coil 18 in the opening defined by flanges 14 and 13, which path is reverse in direction to the flux generated by coil 17. Therefore, the two magnetic fluxes will flow in the same direction through flange 14 and into ferromagnetic fluid 19, wherein the magnetic fluxes will separate into two flux flows, flowing in opposite directions around the submerged portions of coils 17 and 18, and back into coil form 11 at flanges 15 and 13, respectively. It is also to be noted that the relationship of the dimensions of the coil form to the dimensions of the housing and the amount of ferromagnetic fluid contained in the "partially-filled" housing are chosen to optimize low reluctance magnetic flux paths about the coils, such that the paths not pass through air. In the horizontal position, the flux flowing through coil 17 will be of the same magnitude as the flux flowing through coil 18, and therefore, the impedance of coil 17 will be equal to the impedance of coil 18. The foregoing conclusion as to flux and impedance relies on the ideal condition in which the number of windings, or turns of wire in each coil, is the same. It is not necessary that the number of windings be the same since the system can readily be calibrated to account for differences in the number of windings, as it can for wire material differences or any other factors which would impact the magnetic flux and impedance relationship between the first and second primary coils. For the equal windings, horizontal sensor example, the voltage measured at the junction 21 of coil 17 and coil 18 will be one-half of the voltage of the input current source.

Figure 3:
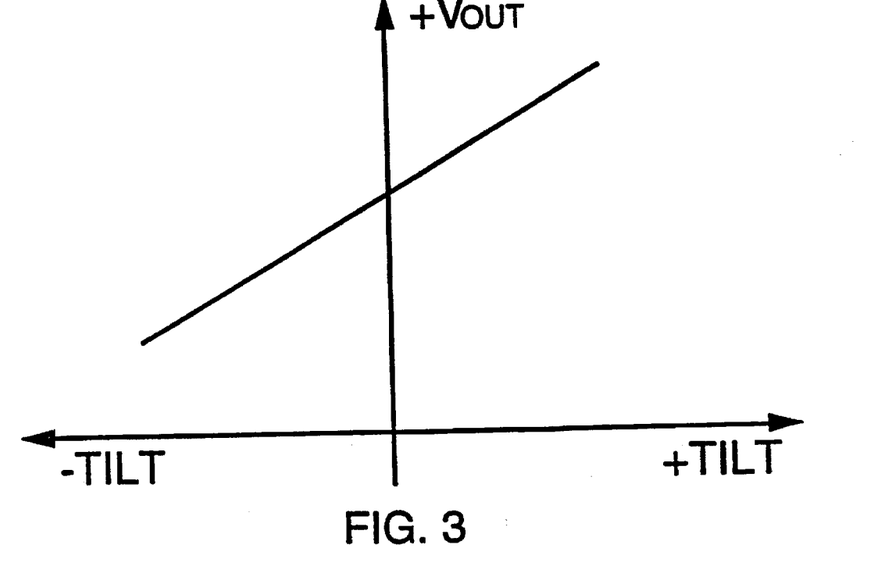
FIG. 3 is a graph illustrating the voltage output: tilt angle relation for the first embodiment and the embodiments shown in FIGS. 15A, 15B and 16 of the invention.

When the tilt sensor 10 is angularly displaced along its longitudinal axis, wherein the bottom surface of the sensor is no longer in a horizontal position, the ferromagnetic fluid 19 will stay horizontal due to gravity. Therefore, the impedance of coil 17 will not be equal to the impedance of coil 18. The voltage measured at the junction 21 of coil 17 and coil 18 will be either lower or higher than the voltage measured at junction 21 when the sensor was in a horizontal position, depending upon the direction of tilt. FIG. 3 provides a graph illustrating the voltage measured at the junction 21 of the coils 17 and 18 as a function of different angles of tilt. Any measured voltage can then be correlated to the respective angle of tilt.

An alternative embodiment of the FIG. 1 sensor 10 has coils 17 and 18 connected in series aiding with the alternating current source connected to the circuit defined by coils 17 and 18. The magnetic flux path generated by coil 17 will flow in the same direction as the magnetic flux path generated by coil 18. In this instance, when the sensor 10 is placed in a horizontal position, there will be no detectable flux through flange 14, since the flux of coil 17 and the flux of coil 18 are equal in magnitude and are flowing in opposite directions through the flange 14 so as to cancel each other. The impedance of coil 17 will be equal to the impedance of coil 18, due to the flux magnitude in coil 17 being equal to the flux magnitude in coil 18. Therefore, the voltage measured at the junction of coils 17 and 18 will be one-half of the voltage of the current source applied to the series circuit defined by coils 17 and 18.

When the series aiding tilt sensor 10 is tilted along its longitudinal axis, the amount of ferromagnetic fluid surrounding coil 17 will be different from the amount of ferromagnetic fluid surrounding coil 18. Therefore, some magnetic flux will flow through flange 14, and the impedance of coil 17 will no longer be equal to the impedance of coil 18. The change in the voltage measured at the junction of coils 17 and 18 will be a function of the tilt, with the increase or decrease of the voltage again being a function of the direction of the angular displacement of the sensor.

Figure 2:
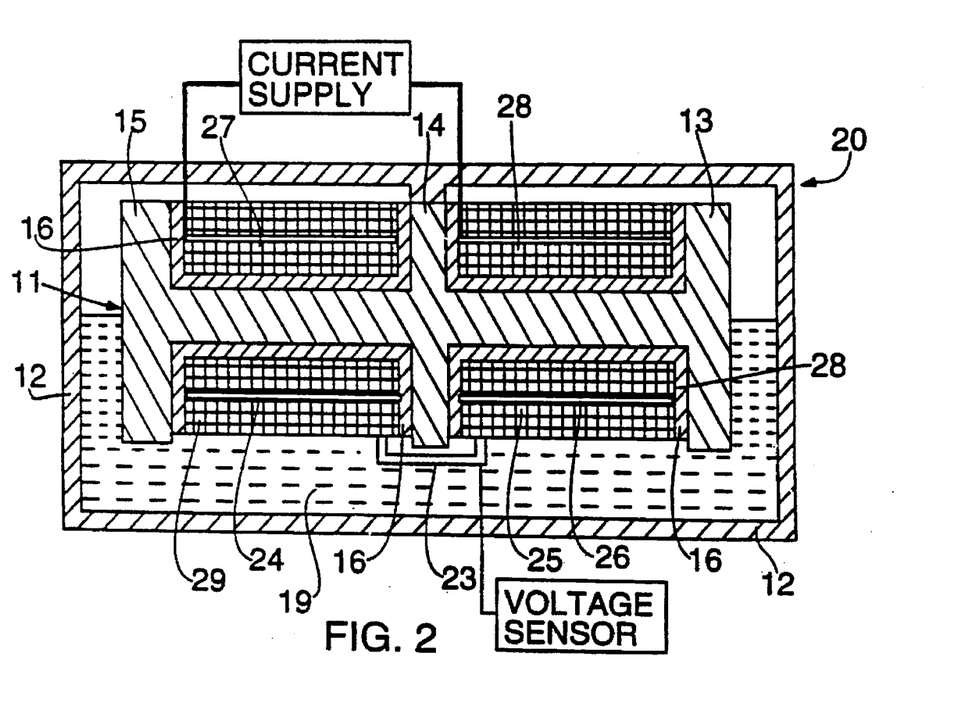
FIG. 2 provides a schematic illustration of a second embodiment of the invention including first and second primary and first and second secondary coils.

In the sensor 10 having first and second primary coils, 17 and 18, whether connected in series opposition or series aiding, the voltage must be correlated from a non-zero point of reference (as is apparent from a review of the graph in FIG. 3), which non-zero point of reference is defined when the sensor is in the horizontal position. To facilitate precise angular measurement, without the need to calibrate the system or correlate the readings output from same, a second embodiment of the invention utilizes pairs Of primary and secondary coils, as illustrated in FIG. 2. With reference to FIG. 2, the tilt sensor, 20 has many of the same basic components as are found in the FIG. 1 embodiment. In order to facilitate understanding of this embodiment and of subsequently-described embodiments of the invention, like reference numerals are utilized for all components which are common to the embodiments, and recitation of the materials, connections, and functions of like components is not repeated, where such would be redundant and readily apparent to one having skill in the art upon a reading of the foregoing.

Referring to FIG. 2, the tilt sensor 20 of this embodiment comprises the ferromagnetic coil form 11 as was described with reference to FIG. 1, including flanges 13, 14 and 15 extending in the radial direction and defining two openings for the coils, with at least flange 14 being attached to housing 12. The openings may be lined with bobbins 16 of insulating material as discussed above. First primary coil 27 of insulated electrically conductive wire is wound about the opening defined by flanges 14 and 15 and is connected in series opposition at junction 22 to second primary coil 28 of insulated electrically conductive wire which is wound about the opening defined by flanges 14 and 13. An interlayer 24 of electrical insulation material, such as electrical tape is disposed about coil 27 and interlayer 26 of the same electrical insulation material is disposed about coil 28. First secondary coil 29 of insulated electrically conductive wire is wound over the interlayer 24, about first primary coil 27, in the opening defined by flanges 15 and 14 and is connected in series aiding at junction 23 to second secondary coil 25 of insulated electrically conductive wire wound over the interlayer 26, about second primary coil 28, in the opening defined by flanges 14 and 13. Sealed housing 12 is partially filled with ferromagnetic fluid 19 such that the coil form 11 is partially submerged in the ferromagnetic fluid.

In operation, a source of alternating current is connected to the terminals of coil 27 and coil 28 which are connected in series opposition causing current through first primary coil 27 to generate a magnetic flux and current through second primary coil 28 to generate a magnetic flux reversed in direction to the flux generated by first primary coil 27. In the horizontal position, therefore, the two magnetic fluxes will flow in the same direction through flange 14, into the ferromagnetic fluid 19, wherein the magnetic fluxes will separate into two equal flux flows, flowing in opposite directions around coil 27 and coil 28, into flanges 15 and 13 respectively, and back into coil form 11.

Since first secondary coil 29 is wound over first primary coil 27, and second secondary coil 25 is wound over second primary coil 28, the flux will pass through coil 29 and coil 25. Since first secondary coil 29 and second secondary coil 25 are connected in series aiding, and the fluxes flow in opposite direction, the voltage generated in coil 29 will cancel the voltage generated in coil 25, when the fluxes have the same magnitude. When the tilt sensor 20 is placed in the horizontal position, the flux flow around first primary coil 27 and first secondary coil 29 will be equal to the magnitude of the flux flow around second primary coil 28 and second secondary coil 25. Therefore, the output voltage measured by a meter connected across the circuit of secondary coils 29 and 25 will be zero. When tilt sensor 20 is tilted along its longitudinal axis, the flat bottom surface of housing 12 will not be in the horizontal position, but the ferromagnetic fluid 19 will stay horizontal due to gravity, and the amount of ferromagnetic fluid 19 between flange 14 and flange 15 will be different from the amount of ferromagnetic fluid between flange 14 and flange 13. Therefore, the voltage measured by a meter connected across the secondary circuit will increase and will be reversed in phase depending upon the direction of tilt.

Figure 4:
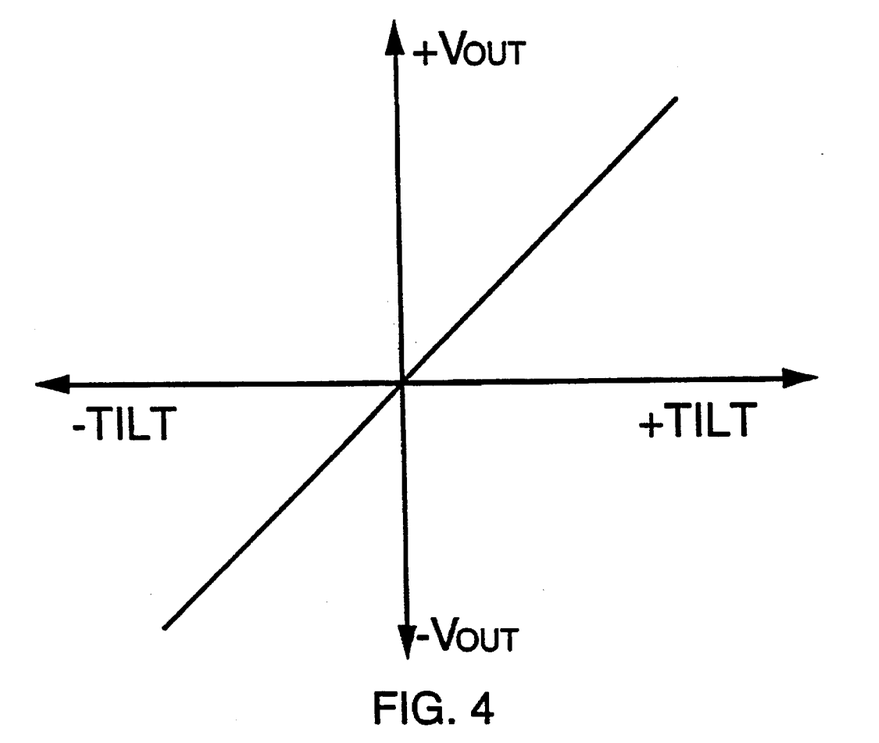
FIG. 4 is a graph illustrating the voltage output: tilt angle for the second embodiment and the embodiments shown in FIGS. 12A, 12B and 13 of the invention.

FIG. 4 provides a graph of the output voltage of the secondary circuit as a function of tilt of the sensor. For this embodiment, a zero output is measured when the sensor is in the horizontal position; a positive voltage is registered when the sensor is tilted in one direction; and, a negative output is registered when the sensor is tilted in the opposite direction.

Figure 5:
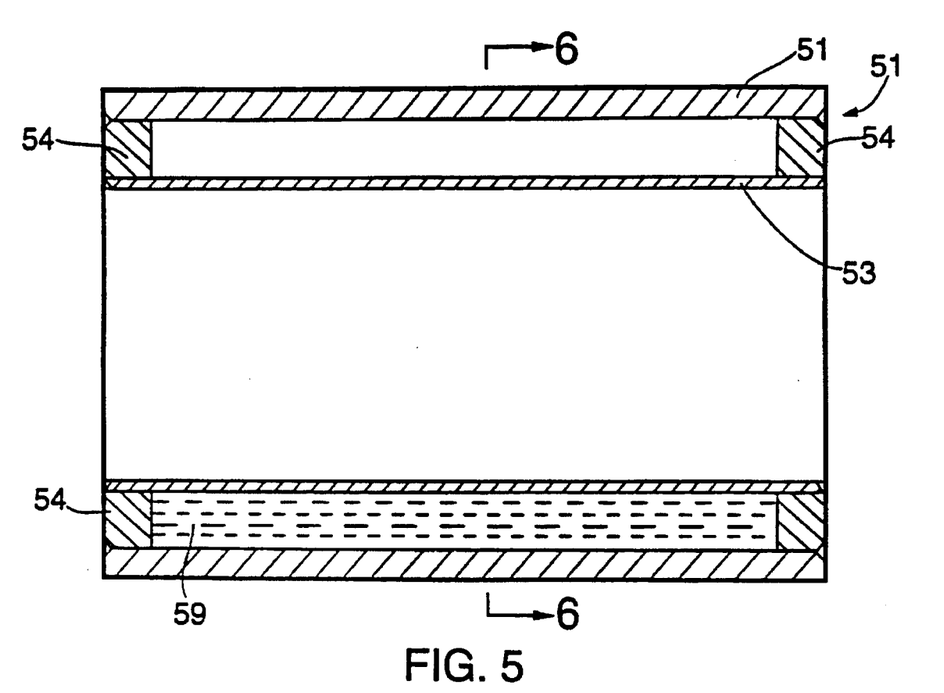
FIG. 5 provides a schematic illustration of the cylindrical member having an annular channel as utilized in several embodiments of the invention.
Figure 6:
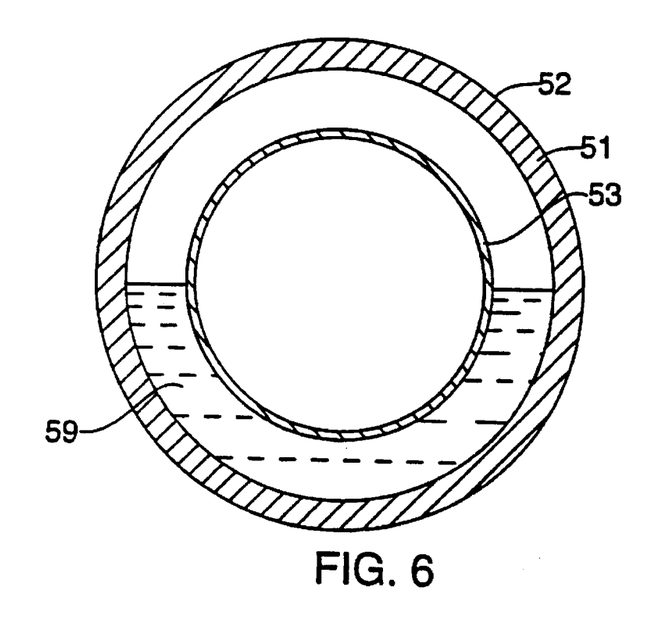
FIG. 6 is a cross-section of the cylindrical member having an annular channel as utilized in several embodiments of the invention.
Figure 7:
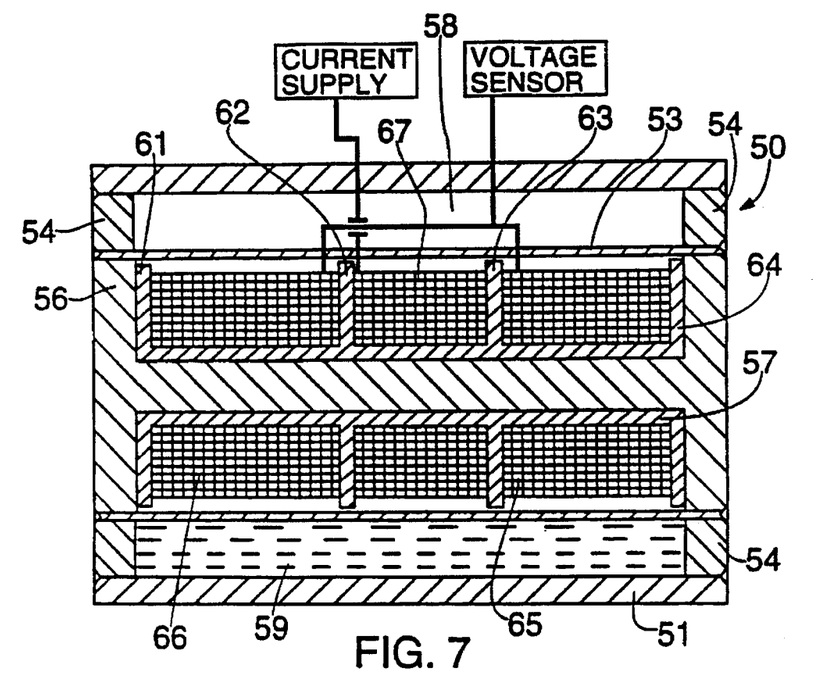
FIG. 7 provides a schematic illustration of the third embodiment of the invention having a single primary and two secondary coils positioned about a frame in the opening defined by the longitudinal axis of a cylindrical member having an annular channel.
Figure 8:
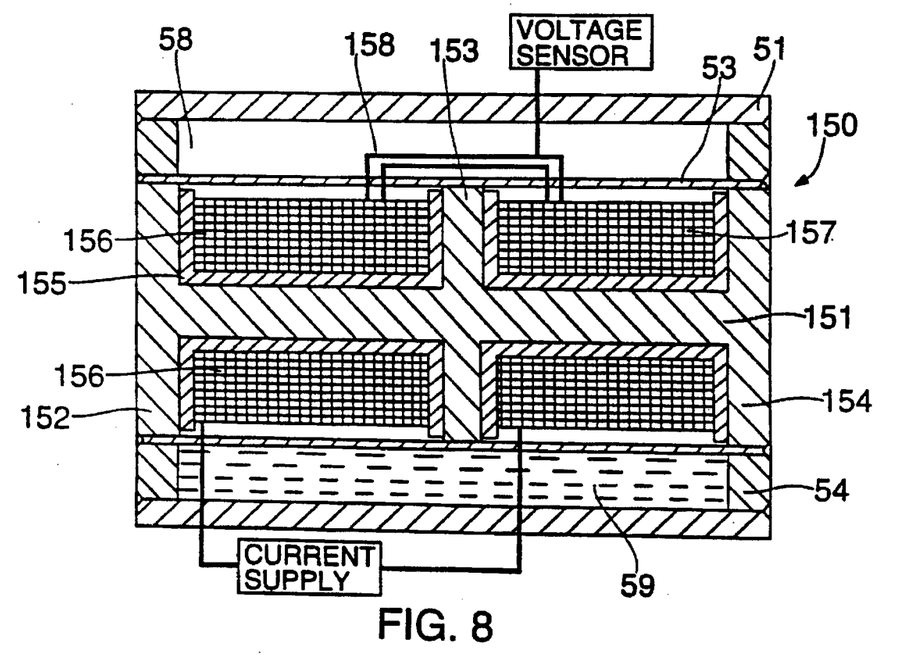
FIG. 8 provides a schematic illustration of a fourth embodiment of the invention having two primary coils positioned about a frame in the opening defined by the longitudinal axis of a cylindrical member having an annular channel.
Figure 9:
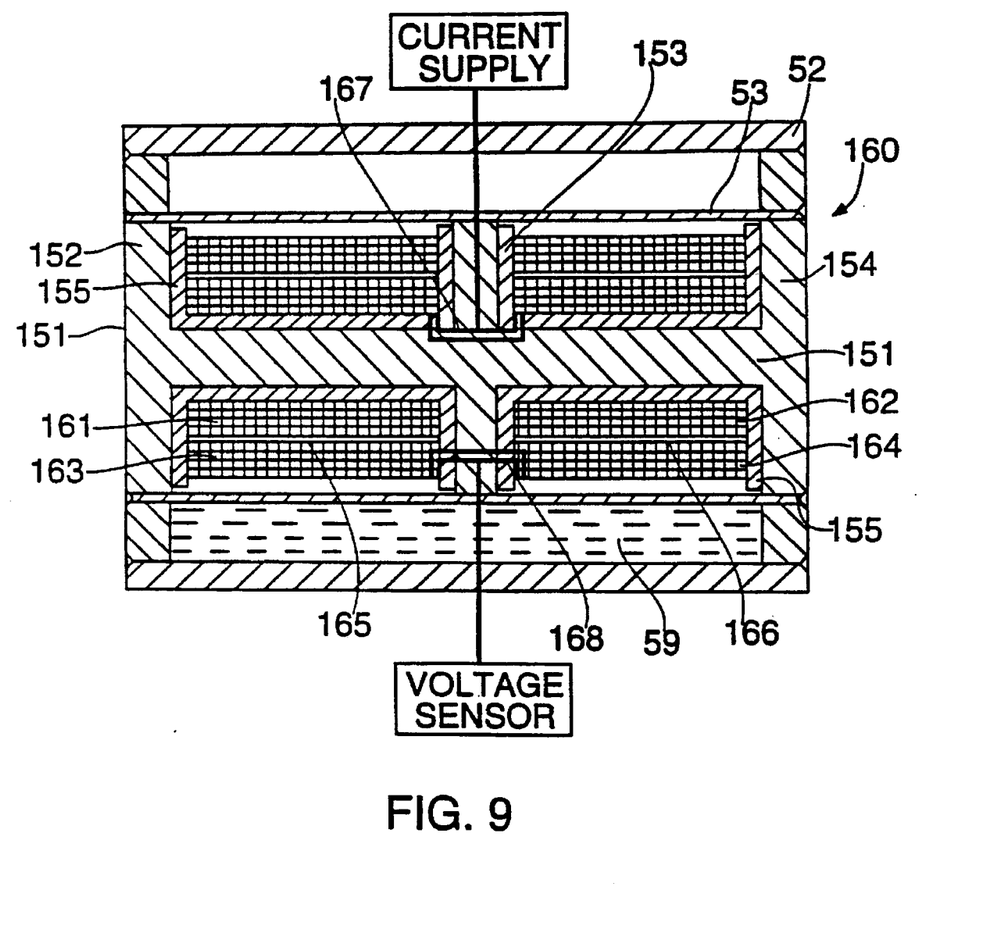
FIG. 9 provides a schematic illustration of a fifth embodiment of the invention having two primary and two secondary coils positioned about a frame in the opening defined by the longitudinal axis of a cylindrical member having an annular channel.

A housing 52 for another embodiment of the inventive tilt sensor is illustrated in FIG. 5. The housing 52 is fabricated of a plastic or non-ferromagnetic metal, such as a non-magnetic stainless steel, and has a circular outer wall 51 and a circular inner wall 53 which define outer and inner circles with an annular space therebetween (see FIG. 6). The housing comprises a cylindrical member having an annular channel between walls 51 and 53, which channel extends along the length 55 of the housing. Each end of the channel is sealed with seal plug 54, effectively a washer fabricated of ferromagnetic material, having a thickness equal to that of the outer wall [or coil form] to optimize the flux path, which is preferably fabricated of the same material as the housing. Ferromagnetic fluid 59 is disposed in the annular channel of housing 52 to partially fill the housing. FIG. 6 provides a cross-sectional view of the housing of FIG. 5 as taken along the plane A—A' of FIG. 5. As detailed with reference to the above-described embodiments, upon angular displacement of housing 52, the surface of the ferromagnetic fluid will remain horizontal under the influence of gravity. FIGS. 7 through 9 illustrate sensor embodiments having housing 52 and utilizing the shifting of a ferromagnetic fluid disposed therein to measure angular displacement of the housing.

FIG. 7 provides a tilt sensor 50 including cylindrical housing 52 having annular channel 58 which is partially filled with ferromagnetic fluid 59, as described with reference to FIG. 5. In the opening defined by the inner wall of the cylindrical housing having the annular channel, coextensive coil form 56 is located along the longitudinal axis of the housing. Coil form 56 has flange ends which fit into the circular ends of the housing cylinder, attaching the coil form to the inner wall of the housing at the ends. Bobbin 57 is disposed about the coil form 56 and has bobbin flanges 61, 62, 63 and 64 which define three compartments or channels along the coil form. Primary coil 67 is wound about the center channel of the sensor, the channel being defined by flanges 62 and 63. As above, the primary coil is preferably an insulated, electrically conductive wire which is connected to receive an alternating current from an AC source (not shown). The alternating current will generate alternating magnetic flux flow through the center axis of coil form 56, through a first flange located at a first end of the coil form, through seal plug 54 at the first end, into and along the ferromagnetic fluid 59, into the seal plug 54 at the opposite end of the sensor, into flange 54 at the opposite end of the coil form, and back along the center axis of the coil form. The tilt sensor 50 is additionally provided with first and second secondary coils, 66 and 65. The first secondary coil, 66, is insulated electrically conductive wire which is wound about the bobbin in the channel defined by bobbin flanges 61 and 62. Second secondary coil 65 of insulated electrically conductive wire is wound about the bobbin in the channel defined by bobbin flanges 63 and 64. The first and second secondary coils are connected to one another in series opposition. Therefore, when an AC current is applied to primary coil 67, the voltage across the secondary circuit of the differential transformer, as measured by a meter connected across the secondary circuit (not shown) will be the result of the flux flow in each of the secondary coils 66 and 65. When the tilt sensor is in a horizontal position, the measured voltage will be zero. When the sensor is tilted, the ferromagnetic fluid will stay level due to gravity and, therefore, as above, the amount of ferromagnetic fluid 59 about one secondary coil will increase and the amount of ferromagnetic fluid about the other secondary coil will decrease, causing a change in the magnetic coupling between primary coil 67 and the secondary circuit. The change in magnetic coupling will cause an output voltage measured across the secondary circuit which voltage is a function of the angular displacement of the sensor along its longitudinal axis.

FIG. 8 provides another embodiment of the invention utilizing the cylindrical housing 52. In the FIG. 8 embodiment, the housing, channel, seal plugs, and ferromagnetic fluid are unchanged from the FIG. 7 embodiment. The coil form and associated coils, however, are configured differently and parallel the FIG. 1 sensor in materials and function. The sensor 150 has coil form 151 having a central axis and flanges 152, 153 and 154 extending radially from the central axis. Flanges 152 and 153 define a first opening in the coil form, while flanges 153 and 154 define a second opening. Bobbins 155 may optionally be included along he openings to provide additional insulation and facilitate winding of the coils. First primary coil 156 is wound about the coil form in the opening defined by flanges 152 and 153 and is connected at junction 158 in series opposition to the second primary coil 157 which is wound about the coil form in the opening defined by flanges 153 and 154. In operation, the FIG. 8 embodiment parallels the FIG. 1 embodiment whereby a non-zero reference value is determined when the sensor is in a first, horizontal position. Upon angular displacement of the sensor 150 along its longitudinal axis, the AC current applied to the primary coil circuit will generate magnetic flux paths as described for sensor 10, such that the impedance of coil 156 will not be equal to the impedance in coil 157 and the voltage measured at junction 158 will be either higher or lower than the non-zero horizontal reference value in an amount which is indicative of the angle of tilt.

FIG. 9 illustrates another embodiment of the invention wherein the cylindrical housing 52 is utilized. In the FIG. 9 embodiment, the coil form 151 has the same configuration as in the FIG. 8 embodiment, wherein flanges 152 and 153 define a first opening and flanges 153 and 154 define a second opening. As with the other sensor embodiments, and particularly the FIG. 2 sensor which parallels the coil form and circuitry of the present embodiment, the openings in the coil form may optionally be provided with bobbins 155 for additional insulation and ease of winding application. A first primary coil 161 is wound about the coil form in the opening defined by flanges 152 and 153, and is connected in series opposition at junction 167 to second primary coil 162 which is wound about the coil form in the opening defined by flanges 153 and 154. Interlayer 165 is provided over first primary coil 161 and interlayer 166 is provided over second primary coil 162, each interlayer being fabricated of electrical tape or like insulating material. First secondary coil 163 is wound over the interlayer 165 in the opening defined by flanges 152 and 153 and is connected at junction 168 in series aiding to second secondary coil 164 which is wound over interlayer 166 in the opening defined by flanges 153 and 154. As noted in the description of the FIG. 1 and FIG. 2 embodiments, the dimensions of the coil form relative to the housing and the amount of ferromagnetic fluid are optimized to provide a low reluctance magnetic path. In the FIGS. 7-9 sensors, the thickness of channel 58 is also selected to provide optimal fluid depth for the paths.

In operation, the FIG. 9 sensor parallels the FIG. 2 embodiment. An AC current applied to the primary circuit generates the magnetic flux paths which pass through the secondary coils. A meter attached across the secondary circuit will detect a zero voltage when the sensor is in the horizontal position due to cancellation of the equal fluxes. Upon angular displacement of the sensor along its longitudinal axis, however, the meter will detect a positive voltage when the sensor is tilted in one direction and a negative voltage when the sensor is tilted in the opposite direction.

Figure 10A:
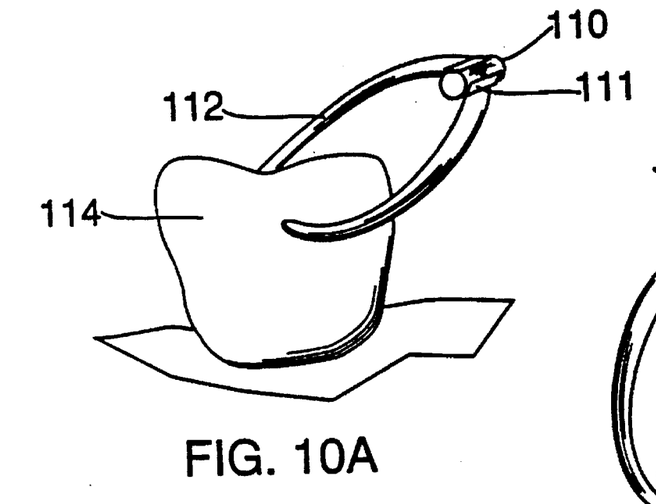
FIGS. 10A and 10B illustrate the inventive sensor mounted in a clamp adapted for attaching to a body, i.e., a tooth, for conducting the inventive angular measurements.
Figure 10B:
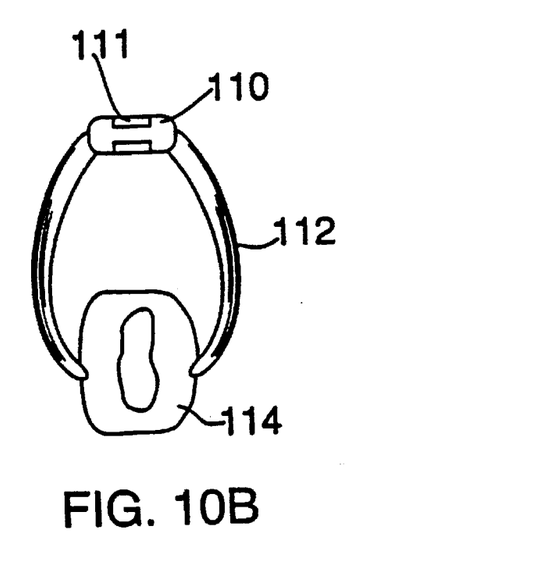

FIGS. 10A and 10B illustrate the inventive sensor mounted in clamps such as rubber dam clamps, adapted to engage a tooth for which angular displacement is to be measured. In FIG. 10A, the sensor 110 is held by a metal clip 111 which is soldered or cemented to clamp 112 which engages the tooth 114 for which angular displacement is to be measured. FIG. 10B provides an overhead view of the same arrangement.

Figure 11:
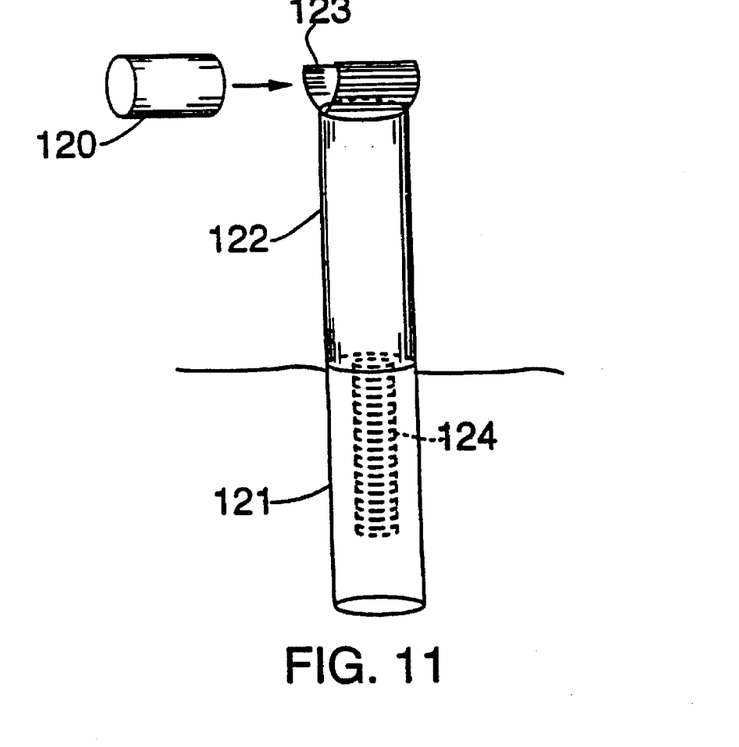
FIG. 11 illustrates the inventive sensor mounted in a member adapted for attaching to a body, i.e., a provisional component, an impression coping, or an abutment on an implanted dental fixture, for which angular displacement is to be measured.

FIG. 11 illustrates the inventive sensor 120 for mounting in a metal clip 123 which is attached-to a member 122 adapted to engage the implant fixture 121 via screw 124 for measuring the angular displacement of the implant fixture. The clip ideally has a central circular opening to allow a screw to slip through to attach member 122 to fixture 121 before the sensor is clipped in place.

Figure 12A:
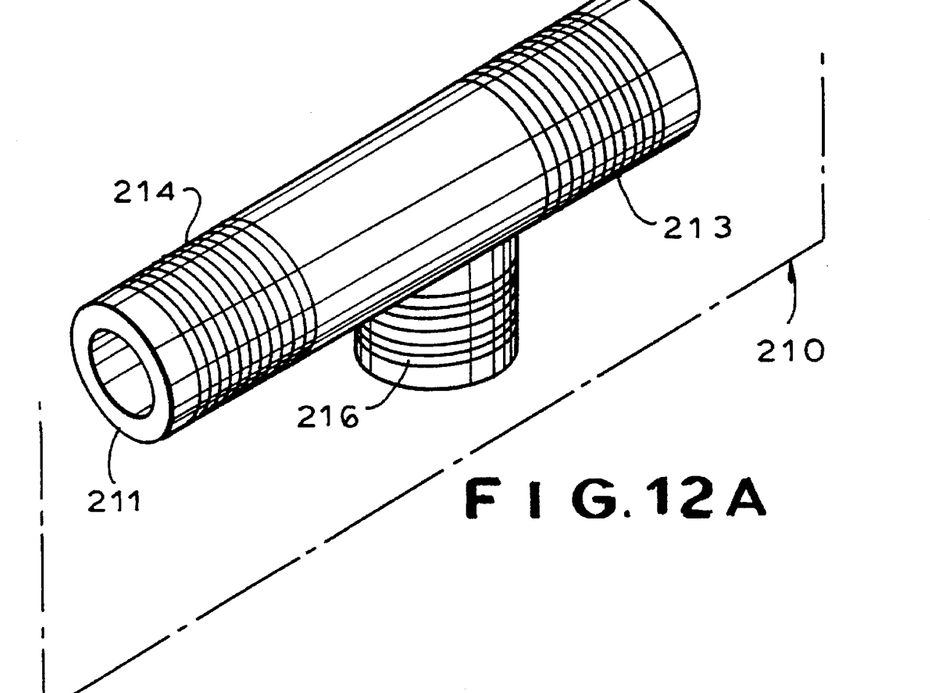
FIGS. 12A and 12B provide perspective and cross-section views of a single axis tilt sensor utilizing a T-shaped coil form.
Figure 12B:
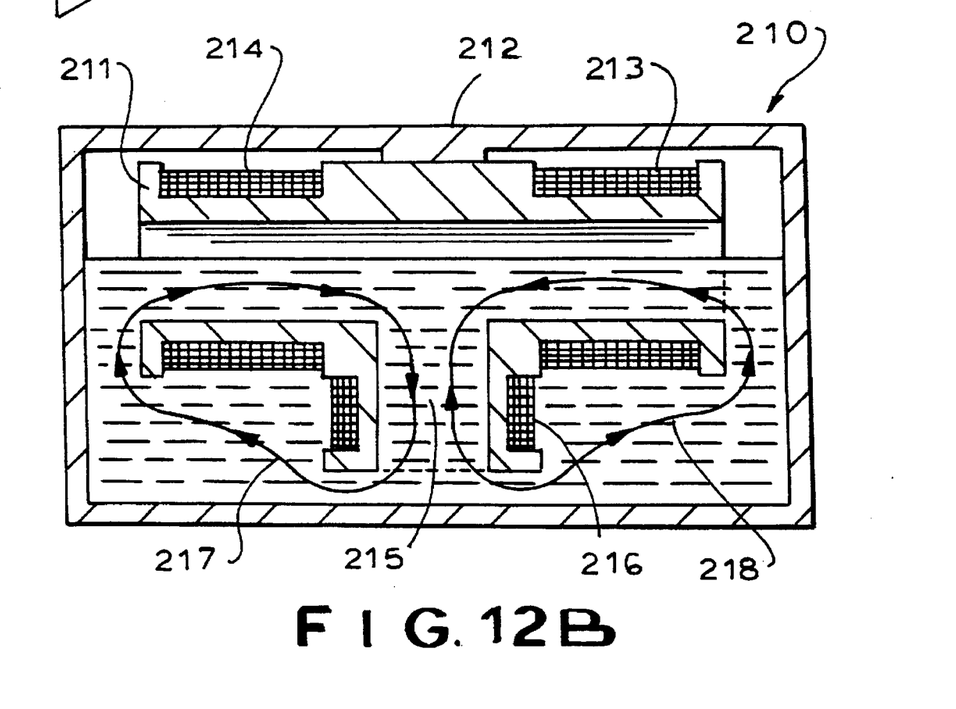

As illustrated in FIGS. 12A and 12B, a further embodiment of a tilt sensor 210 is provided which includes a hollow T-shaped, coil form 211. Coil form 211 is a single unit, as is most apparent from FIG. 12A, comprised of a non-magnetic or non-conductive material such as plastic. The hollowed sections of the form are representatively cylindrical in shape and form a T-shaped cavity with openings at each of the three extremities of the T form. The horizontal extensions of the T form must be equal in length. A primary coil 216 is wound about the central cylindrical vertical portion of the T form and two secondary coils 213 and 214 are wound on the horizontal portions of the T form, with one coil wound about the horizontal portion on each side of the center cylindrical vertical portion. The number of windings for each of the two secondary coils must be equal. All of the coils are electrically insulated conductive wire.

In the FIG. 12A and 12B embodiment of the invention, the two secondary coils are connected in series-aiding. As described above, insulated bobbins may be disposed on the vertical and horizontal portions of the T form to provide insulation and to facilitate winding of the coils about the form. The hollow T-shaped coil form is secured to the upper wall of a sealed housing 212 and is aligned such that the horizontal portions are parallel to the longitudinal axis of the sensor housing. Housing 212 is partially filled with ferromagnetic fluid 215 to a level at which the secondary coils are contacted and submersed in the fluid to the central longitudinal axis of the coils. The housing is comprised of an electrically and magnetically inert material such as plastic or a non-ferromagnetic metal. When the sensor assembly is placed on a horizontal plane (i.e., the T form in an upright position) the axis of the coils wound over the horizontal portions of the T form is parallel to the horizontal plane and the level of the ferromagnetic fluid reaches the central longitudinal axis of the two secondary coils.

When an alternating current power source is connected to the terminals (not shown) of the primary coil wound about the vertical portion of the hollowed T form, an alternating magnetic flux will be generated in the surrounding ferromagnetic fluid. As illustrated by flux paths 217 and 218, the magnetic flux will be divided into two equal parts and will flow in opposite directions (i.e., as illustrated, clockwise along flux path 217 and counterclockwise along flux path 218), through the two secondary coils, and back into the single primary coil of the transformer.

The two secondary coils, 214 and 213 wound about the horizontal portions of the hollowed coil form, are connected in series aiding to each other and form the secondary circuit of the transformer. At the horizontal position of the axis of the secondaries, the amounts of ferromagnetic fluid in the secondaries will equal each other; and, therefore, the flux density in secondary 213 will be equal to the flux density in secondary 214 and the magnitude of the voltage induced in secondary 213 will be equal to the magnitude of the voltage induced in secondary 214. Since secondary 213 and secondary 214 are connected in series aiding, and the flux in the secondary coils flows in opposite directions, the net output voltage measured by sensing means connected at the terminals (not shown) of the secondary circuit will be zero when the sensor is in the horizontal position.

Figure 17:
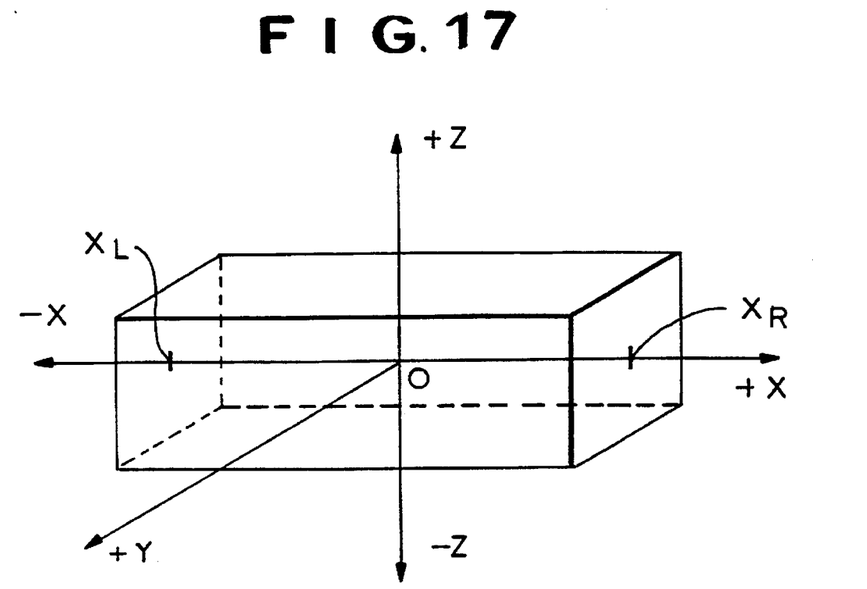
FIG. 17 is a geometrical schematic of the tilt sensors shown in FIGS. 12A and 12B and FIGS. 15A and 15B.

When the sensor is tilted, the level of the ferromagnetic fluid will stay horizontal due to gravity. Thus, there will be an increase in the amount of fluid surrounding one secondary coil and a decrease in the amount of fluid surrounding the other secondary coil. The level of magnetic flux will change accordingly and a differential voltage will be generated at the terminals of the secondary circuit. In the instance of sustained tilt, rather than an instantaneous response due to acceleration, deceleration or mechanical shock, the voltage will be a function of the tilt angle, and can be used to measure the degree of tilt. FIG. 17 schematically illustrates the planar orientation of the tilted sensor. Referring to FIG. 17, when the sensor is tilted away from the horizontal position in the X-Z plane, Xr moving in the direction of –Z, the amount of fluid 215 at secondary 213 will increase and the amount of fluid 215 at secondary 214 will decrease. Therefore, the output voltage measured across secondary 214 will decrease. Since secondary 213 and secondary 214 are connected in series aiding, the flow of flux in secondary 213 is reverse in direction to the flow of flux in secondary 214 and the voltage measured across secondary 212 will be reverse in phase to the voltage measured across secondary 214. The series output voltage measured across the secondary circuit will, therefore, be the difference between these two voltages. When the sensor is tilted at the same angle in the opposite direction, XL rotated in the –Z direction on FIG. 17, the magnitude of the output voltage will change proportionately but will be reverse in phase to the voltage measured due to the rotation Xr.

Figure 13:
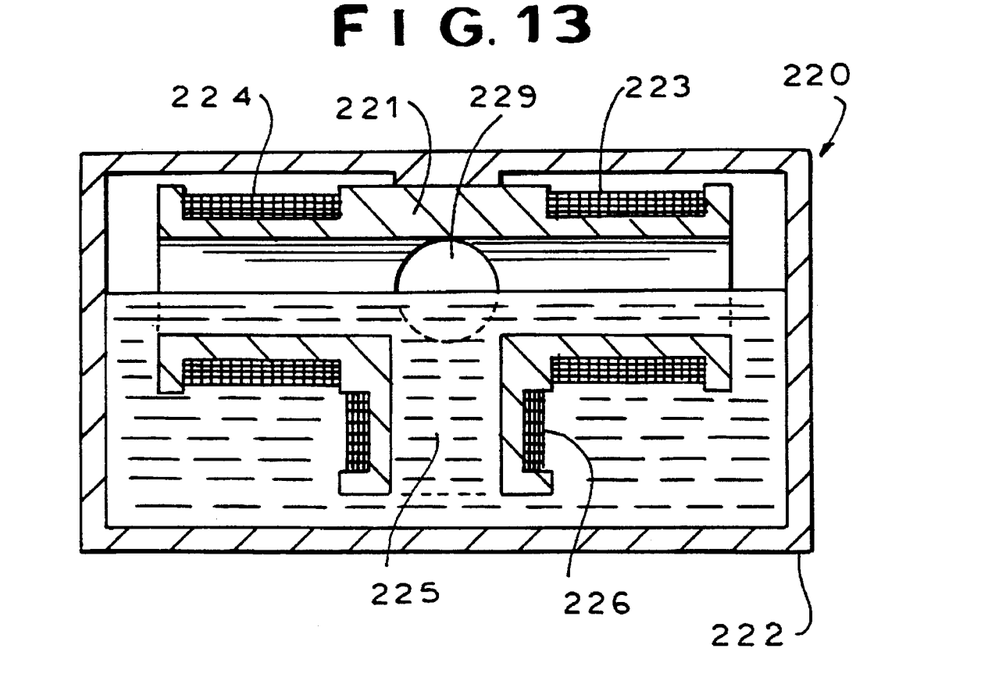
FIG. 13 is a longitudinal section of a dual axis tilt sensor utilizing a double T-shaped (or "+" shaped) coil form.
Figure 14:
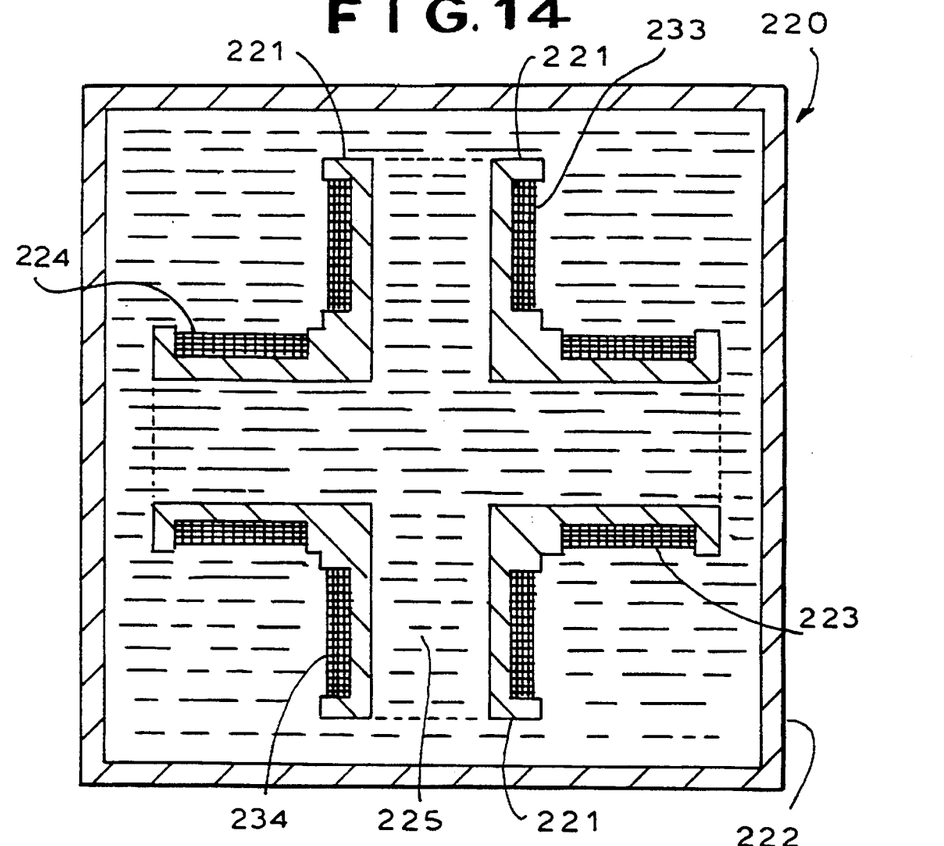
FIG. 14 is an overhead view of the tilt sensor of FIG. 13 viewed at a level below the surface of the ferromagnetic fluid.

The hollow T form design can be applied to a dual-axis tilt sensor by adding two additional hollow horizontal arms to the T-shaped coil form in the same plane as and perpendicular to the first set of horizontal arms, to result in a hollow "+" form. The dual axis sensor as illustrated in FIGS. 13 and 14, is comprised of two sets of horizontal coils, 223 with 224 and 233 with 234, oriented on the sets of arms which are perpendicular to each other, one vertical primary coil 226, coil form 221 on which the coils are wound, and housing 222 partially filled with ferromagnetic fluid 225. A tilt from the horizontal plane of one set of secondaries will not affect the other set since the sets are in the same plane as each other. The overview perspective of FIG. 14 shows the two additional secondary coils 234 and 233 wound with insulated electrically conductive wire over the additional horizontal extensions of coil form 221, with secondary coil 234 and secondary coil 233 being connected in series aiding. The central longitudinal axis of the pair comprising secondary coil 223 and secondary coil 224 is perpendicular to the central longitudinal axis of secondary coil 233 and secondary coil 234, and both axes are disposed in a plane parallel to the longitudinal axis of the sensor and perpendicular to the axis of the vertical portion about which primary coil 226 is wound.

Figure 18:
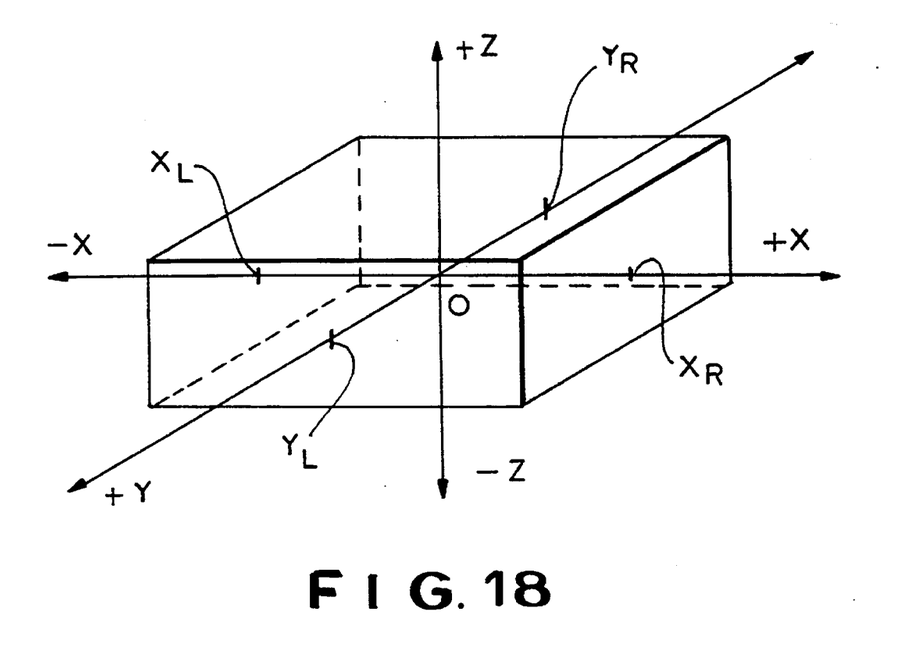
FIG. 18 is a geometrical schematic of the tilt sensors shown in FIGS. 13, 14 and 16.

The principle of operation of the tilt sensor shown in FIGS. 13 and 14 is the same as the tilt sensor shown in FIG. 12B; however, angular displacement can be detected not only for X-Z plane displacement but also for Y-Z plane displacement. Referring to FIG. 18, a tilt of the sensor in the X-Z plane, Xr and XL moving in the direction of the Z axis, will produce an output voltage for the circuit formed by the series aiding connection of secondary coil 223 and secondary coil 224, and will not produce an output voltage for the circuit formed by the series aiding connection of secondary coil 233 and secondary coil 234, since the amount of fluid 225 at secondary coil 233 and secondary coil 234 may change, but will remain constant with respect to the pair. On the other hand, when the sensor is tilted in the Y-Z plane (i.e., Yr and YL moving in the direction of the Z axis), the circuit formed by secondary coil 233 and secondary coil 234 will produce an output.

For applications where a differential transformer configuration is not required, the primary coil can be eliminated and the power source applied to the terminals of the secondary coils connected in series opposition. These coils will form a voltage divider and the voltage output will be measured at the junction of the two coils, as above in the FIG. 1 embodiment. Clearly, the paired coils can be referred to as primary coils in this embodiment; however, for the sake of consistency, the term "secondary" will be maintained. At the horizontal position, the amount of ferromagnetic fluid at each secondary will be equal to the amount at the other and, therefore, the impedance of each of the two coils will be equal. When the assembly is tilted, the amount of ferromagnetic fluid surrounding one secondary coil will increase and the amount of ferromagnetic fluid surrounding the other secondary will decrease causing a change in the divided voltage with the change being a function of the tilt angle.

Figure 15A:
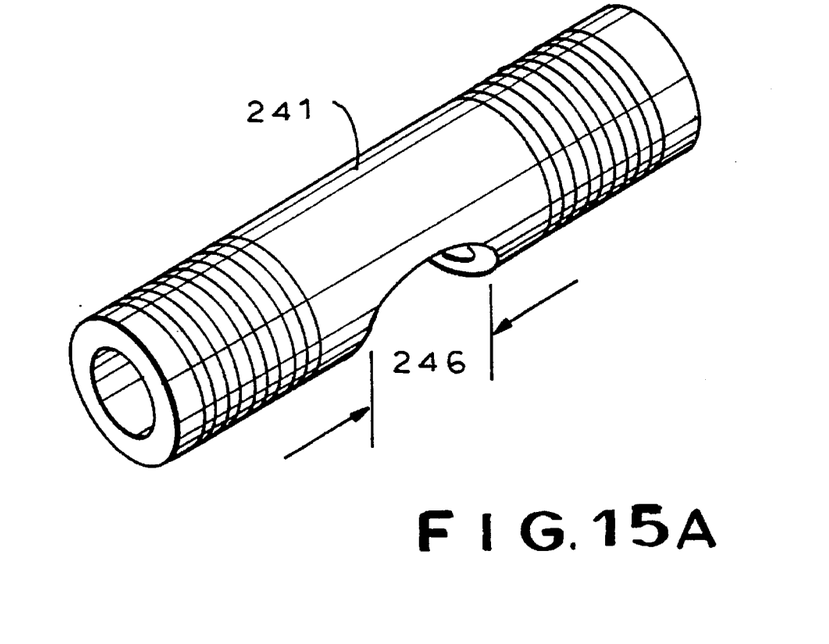
FIGS. 15A and 15B provide perspective and cross-section views of a single axis tilt sensor utilizing a hollow cylindrical coil form.
Figure 15B:
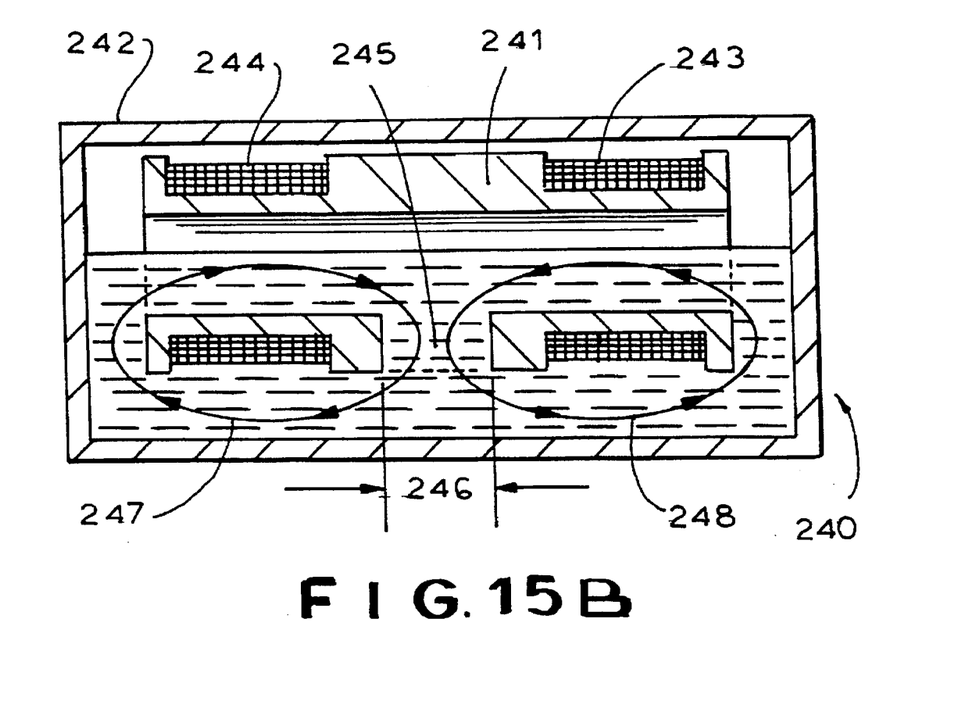

Referring to FIGS. 15A and 15B of the drawings, a single-axis sensor 240 comprised of a voltage divider is illustrated. The sensor includes elongated coil form 241, hollowed through its entire length and made of non-magnetic material which form has a radial opening 246 at the center of the lower surface of the cylinder, with the radial opening 246 being centered along the axial length of the cylindrical coil form 241. Two coils 243 and 244 of insulated electrically conductive wire are wound about each end of the hollowed coil form 241. Coils 243 and 244 are connected in series opposition. As above, the housing 242 is made of solid and stable material such as metal or hard plastic and the coil form 241 is secured to the inner top of the housing with the central longitudinal axis of said coil form parallel to the longitudinal axis of the housing. Ferromagnetic fluid 245 partially fills the housing and contacts the coil form 241 to about the level of the center axis of coils 243 and 244 when the sensor is in the horizontal position. The embodiment of FIGS. 15A and 15B electrically parallel the FIG. 1 coil arrangement about the hollow cylinder.

In operation, a source of alternating electrical current is connected to the circuit comprising coils 243 and 244 circuit. When the sensor is placed in the horizontal position and the axes of coil 243 and coil 244 are parallel to the longitudinal axis of the housing 247, the amount of ferromagnetic fluid 245 at coil 243 will be equal to the amount of ferromagnetic fluid at coil 244. The electrical current will generate a magnetic flux in coil 243 that will oppose the magnetic flux generated by the electrical current in coil 244, due to the fact that the coils are connected in series opposition. Therefore, the magnetic flux paths will flow through coil 243 and coil 244 in opposite directions, and will be united at opening 246 to become one flux path. The flux will flow out of opening 246 and be separated into two equal flux flows flowing back into the extremities of coil form 241. At the horizontal position, the electrical inductance of coil 243 will be equal to the electrical inductance of coil 244, and the voltage measured between the solder joint (not shown) of coil 243 and coil 244 and each terminal of said circuit will be equal to ½ of the voltage applied to said circuit terminals.

Referring to FIG. 17, when the sensor is tilted away from the horizontal position, Xr rotated in the X-Z plane in the direction of –Z, the amount of fluid 245 at coil 243 will be increased, and the amount of fluid 245 at coil 244 will be decreased. Therefore, the electrical impedance of coil 243 will be increased and the electrical impedance of coil 244 will be decreased. The voltage measured between the solder joint of coil 243 and coil 244, and the terminal of coil 243 will increase, since the input current from the power source is constant and is equal to the input voltage divided by the total impedance of the circuit. The voltage measured across the circuit will be equal to the multiplication of the input current by the impedance of coil 243 as illustrated in FIG. 3 of the drawings. Referring again to FIG. 17, when the sensor is tilted such that XL is rotated in plane X–Z in the direction of –Z, the amount of fluid 245 at coil 243 will be reduced, and the amount of fluid 245 at coil 244 will be increased. Therefore, the voltage measured between the solder joint of coil 243 and coil 244 and the said input terminal of coil 243 will be decreased (see FIG. 3 of the drawing).

This design can be applied to a two axis tilt sensor as described with reference to FIG. 16 wherein sensor 250 comprises housing 252, coil form 251 (which from an overhead view will correspond with the form illustrated in FIG. 14), two sets of coils 254 and 253 (shown in FIG. 16) and 264 and 263 (not shown in FIG. 16) wound about the perpendicularly-oriented arms of coil form 251, and ferromagnetic fluid 255 partially filling housing 252, to a level at which all coils are contacted with fluid when the sensor is in a horizontal position and the fluid reaches the mid-point of the horizontal coils.

Figure 16:
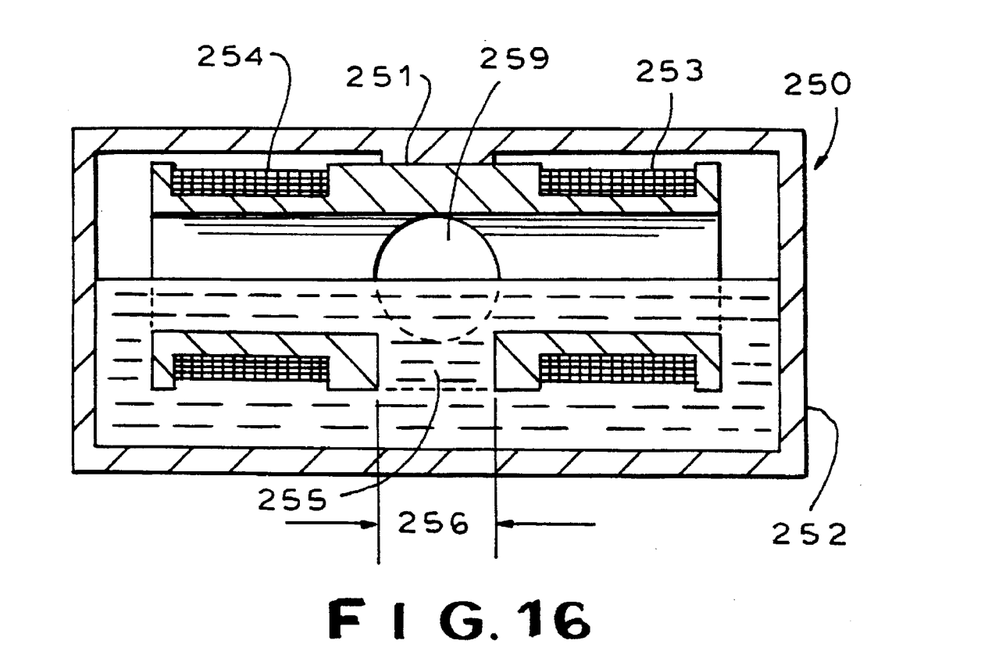
FIG. 16 is a longitudinal section of a dual axis tilt sensor utilizing a dual hollow cylindrical coil form.

In FIG. 16, an elongated coil form 251, hollowed through its entire length and made of non-magnetic material, has a radial opening 256 located at about the mid-point of coil form 251. Two coils 253 and 254 comprising insulated, electrically conductive wire are wound, one at each end of hollowed coil form 251, and are connected in series opposition. Sealed housing 252 is made of solid and stable material such as non-ferromagnetic metal or hard plastic to which the coil form 251 is secured at the inner top of the housing. The axes of coils 253 and 254 are parallel to the longitudinal axis of the sensor. In addition, coil form extensions having coils 263 and 264 (not shown) are oriented perpendicular to and in the plane of the extensions having coils 253 and 254. Coils 263 and 264 are connected to each other in series opposition. Ferromagnetic fluid 255 partially fills the housing to a level up to the midpoint of coils 253, 254, 263 and 264. Also shown in FIG. 16 of this drawing is cavity 259 of the perpendicular part of the coil form 251 which represents the center point of the "+" shape formed by the four extremities.

Referring again to FIG. 14, the overhead view of the dual axis tilt sensor 220 corresponds to the overhead view of the embodiment illustrated in FIG. 16. Each pair of electrically conductive wire wound about the perpendicular extensions of coil form 251, coils 253 with 254 and coils 263 with 264, is connected in series opposition. The axis of the pair of coils 253 and 254 is perpendicular to the axis of the pair of coils 263 and 264 and both axes are located on a plane parallel to the horizontal axis of the sensor.

The principle of operation of tilt sensor shown in FIG. 16 is the same as the tilt sensor shown in FIG. 15B. Referring to FIG. 18, a tilt of the sensor in the X-Z plane, Xr and XL moving in the direction of the Z axis will produce a change in the voltage measured between the solder joint (not shown) of coils 253 and 254 and the terminals of coil 253 and coil 254, respectively, and will not produce a change in the voltage measured at the solder joint of coil 263 and coil 264 and the terminals of coils 263 and 264, since the amount of fluid 255 at coils 263 and 264 will change, but will remain constant with respect to each other.

Similarly, in response to angular displacement in the Y-Z plane, the voltage measured between the solder joint (not shown) of coils 263 and 264 and the terminals of coil 263 and coil 264 will change when the dual axis tilt sensor is tilted in the Y-Z plane, Yr and YL moving in the direction of the Z axis. In that instance, the voltage measured between the solder joint of coils 253 and 254 and the terminals of coils 253 and 254 will not change.

As referred to previously, FIG. 17 is a geometrical schematic of a single axis tilt sensor of this invention. The 0 point of origin of the X, Y, Z coordinates is located at the center of gravity of the tilt sensor. When the 0 point is stationary, the sensitive plane of rotation is the X-Z plane. The single axis sensor will not, however, generate an output voltage when rotated in the Y-Z plane.

FIG. 18 is a geometrical schematic of the inventive dual axis tilt sensors. The 0 point of origin of the X, Y, Z coordinates is located at the center of gravity of the tilt sensor. When the 0 point is stationary, rotation of the sensor in the X-Z plane will generate an output voltage measured at the X-Z secondary circuit, and no output will be generated at the perpendicular (Y-Z) secondary circuit. Rotation of the sensor in the Y-Z plane will generate an output voltage measured at the Y-Z secondary circuit, and no output will be generated at the perpendicular X-Z secondary circuit.

Referring again to FIGS. 16, 17 and 18, the selection of the center of gravity for the 0 point of origin of the X, Y, Z coordinates was made for the purpose of describing the operation of the tilt sensor. The 0 point of the origin of the X, Y, Z coordinates can be located anywhere on the longitudinal axis of the sensor. Each of the foregoing dual-axis tilt sensors can ascertain tilt at various angular orientations (i.e., tilt in more than one plane at a time) by calculating the tilt from the output voltages of the dual axis perpendicular sensor, for example, by determining the vector sum of the sensed changes.

Figure 19:
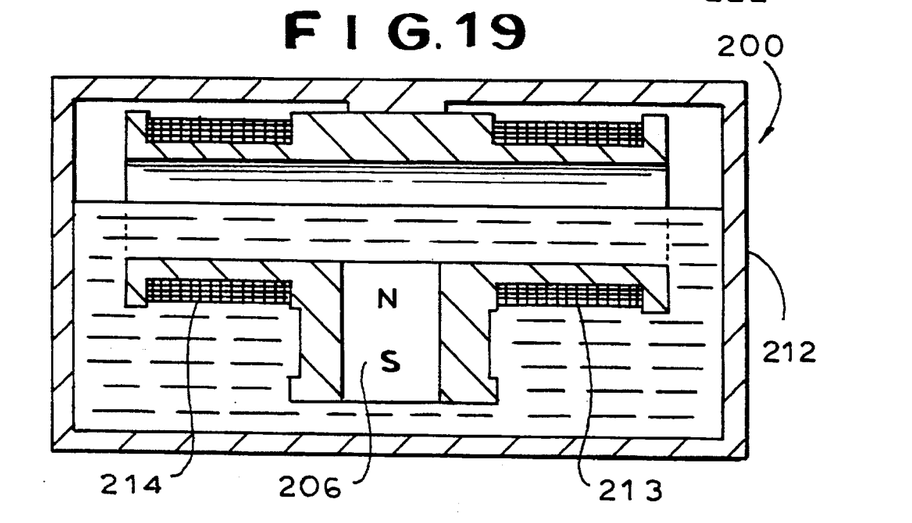
FIG. 19 provides an illustration of the sensor shown in 12B wherein the primary coil has been replaced by a permanent magnet.

A further embodiment 200 as illustrated in FIG. 19, provides for the use of a permanent magnet 206 in the vertical portion of the T form. The permanent magnet is cylindrical or other appropriate shape to fully occupy the vertical portion which previously had been filled with ferromagnetic fluid and which had previously had a primary coil wound about its perimeter. The north and south poles are located on the vertical axis of the vertical portion of the T as shown. Clearly, as will be apparent to one skilled in the art, the poles can be reversed provided that the poles are still vertically oriented. In operation, a constant magnetic flux will flow from one pole of the permanent magnet, through the two coils 213 and 214, into the ferromagnetic fluid and back to the opposite pole. Since the magnetic flux is constant, no voltage will be generated in the secondary coils. Under displacement conditions (e.g., sudden vibration, shock, acceleration, deceleration, etc.), the ferromagnetic fluid will be displaced with respect to the coils causing a change in the magnetic flux and a consequent output voltage at the terminals of the secondary coils. One can provide a single coil on one of the horizontal sections of the T form and still obtain an output voltage on the one secondary coil.

Similarly, a permanent magnet can be provided in the vertical portion of the coil form of the dual axis sensor shown in FIG. 13. As in the FIG. 19 embodiment, the permanent magnet replaces the primary coil and provides a self-generating sensor which does not require an external power source for detecting movement in either of two perpendicular axes. The self-powered sensor is particularly useful for monitoring systems, such as car anti-theft devices, which preferably do not require a constant drain on the primary power source for the monitored equipment.

The sensors of the present invention can be adapted for a wide variety of monitoring needs. Moreover, the output voltage from the dual coil pair circuit can be provided for a variety of applications. For example, a sustained output voltage can be provided to a processor for determination of the exact angle of tilt to be measured. In the alternative, the output voltage can be provided to an associated alarm or other warning system for signaling detection of an instantaneously monitored condition. Yet another application of the output voltage would be to provide input to circuitry adapted to automatically compensate for the angular displacement or other detected condition. In the context of the use of tilt sensors in dentistry, as detailed above, a tilt sensor can be connected to a drill in order to instantaneously compensate for a patient's jaw movement during any drilling procedures which require precise angular orientation.

Although the inventive sensor has been described with specific reference to several embodiments and mountings, it will be apparent to one having skill in the art, upon a reading of this patent, that modifications and materials adjustments may be effected without departing from the spirit and scope of the invention as defined by the appended claims.

What is claimed is:

1. A sensor for sensing displacement of a body comprising:

a sealed housing;

at least one current path means disposed in said housing;

means for applying current to said current path means;

variable low reluctance magnetic flux path about said current path means, comprising a hollow non-ferromagnetic frame disposed in said housing, said frame comprising a vertical portion mounted at the center of the inside floor of said housing and at least one pair of horizontal portions disposed at the top of said vertical portion in a plane perpendicular to said vertical portion, said plane being parallel with the longitudinal and latitudinal axes of said housing, about which frame said at least one current path means is disposed, and ferromagnetic fluid disposed in said sealed housing, in which fluid said frame is partially submerged, the level of said fluid relative to said current path means varying in response to displacement along the axes of said sensor; and sensing means for measuring the output from said current path means as a function of variations in said variable magnetic flux path.

2. The sensor of claim 1 wherein said at least one current path means comprises primary circuit.

3. The sensor of claim 2 wherein said primary circuit comprises a primary coil disposed about said vertical portion of said frame.

4. The sensor of claim 2 wherein said primary circuit comprises at least one pair of primary coils, disposed about each of said at least one pair of horizontal portions of said frame.

5. The sensor of claim 4 wherein each of said at least one pair of primary coils are connected in series opposition.

6. The sensor of claim 3 further comprising a secondary circuit comprising at least one pair of secondary coils disposed about said at least one pair of horizontal portions of said frame, said at least one pair of secondary coils being connected in series aiding.

7. The sensor of claim 6 wherein said means for applying current is connected to said primary circuit and said sensing means is connected to said secondary circuit.

8. The sensor of claim 4 wherein said sensing means comprises at least one sensing means connected to each of said at least one pair of primary coils, and wherein said at least one sensing means produces a sensed output related to said displacement, further comprising means for selectively combining the sensed outputs to determine the amount and direction of displacement of said sensor.

9. The sensor of claim 1 wherein said means for applying current comprises a permanent magnet disposed in said vertical portion of said frame, said magnet having its north and south poles vertically disposed with respect to each other, and wherein said current path means comprises at least one pair of coils disposed about said at least one pair of horizontal portions of said frame, each of said at least one pair of coils being connected in series opposition.

10. The sensor of claim 6 wherein said sensing means comprises at least one sensing means connected to each of said at least one pair of secondary coils, and wherein said at least one sensing means produces a sensed output related to said displacement, further comprising means for selectively combining the sensed outputs to determine the amount and direction of displacement of said sensor.

11. The sensor of claim 1 wherein said means for applying current comprises a permanent magnet disposed in said vertical portion of said frame, said magnet having its north and south poles vertically disposed with respect to each other, and wherein said current path means comprises at least one coil disposed about said at least one horizontal portion of said frame.

12. A method method for sensing displacement of a body with a sensor comprising current path means and variable low reluctance magnetic flux path means, said flux path means comprising ferromagnetic fluid, the level of which in relation to said current path means varies in response to displacement of said sensor, and wherein said current path means comprises two pairs of coils wound about two pairs of horizontal frame portions, said pairs of horizontal frame portions being in a common plane and perpendicular to each other and wherein said sensing means comprises two sensing circuits, one connected to each of said two pairs of coils for producing an output related to the level of said ferromagnetic fluid in relation to said current path means, comprising the steps of:

applying an alternating current to said current path means;

sensing the output of said two sensing circuits as a function of variation in said variable low reluctance magnetic flux path means due to displacement of the sensor and the consequent displacement of said ferromagnetic fluid; and selectively combining the output of said two sensing circuits to determine the amount and direction of displacement of said sensor.

* * * * *